(12) United States Patent
Jones et al.

(10) Patent No.: US 10,130,454 B2
(45) Date of Patent: Nov. 20, 2018

(54) VACCINE DELIVERY DEVICES

(71) Applicant: Iowa State University Research Foundation, Inc., Ames, IA (US)

(72) Inventors: Douglas E. Jones, Kelley, IA (US); Matthew Brewer, Ames, IA (US); Balaji Narasimhan, Ames, IA (US); John Jackman, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 561 days.

(21) Appl. No.: 14/814,148

(22) Filed: Jul. 30, 2015

(65) Prior Publication Data

US 2016/0030146 A1 Feb. 4, 2016

Related U.S. Application Data

(60) Provisional application No. 62/121,040, filed on Feb. 26, 2015, provisional application No. 62/032,475, filed on Aug. 1, 2014.

(51) Int. Cl.
| | |
|---|---|
| *A61D 1/02* | (2006.01) |
| *A61K 9/00* | (2006.01) |
| *A61K 47/42* | (2017.01) |
| *A61K 39/00* | (2006.01) |
| *A61M 5/00* | (2006.01) |

(52) U.S. Cl.
CPC ............ *A61D 1/025* (2013.01); *A61K 9/0024* (2013.01); *A61K 39/0005* (2013.01); *A61K 47/42* (2013.01); *A61K 2039/552* (2013.01); *A61M 5/00* (2013.01)

(58) Field of Classification Search
CPC .. A61D 1/025; A61K 9/0024; A61K 39/0005; A61K 47/42; A61K 2039/552; A61M 5/00
See application file for complete search history.

(56) References Cited

U.S. PATENT DOCUMENTS

| | | | | |
|---|---|---|---|---|
| 4,948,726 | A * | 8/1990 | Longoria | G01N 33/538 435/14 |
| 7,534,607 | B1 * | 5/2009 | Chen | C12N 5/0657 424/93.7 |
| 8,449,916 | B1 * | 5/2013 | Bellaire | A61K 9/14 424/489 |
| 2009/0136527 | A1 * | 5/2009 | Millar | C07K 7/06 424/185.1 |

(Continued)

OTHER PUBLICATIONS

Beekman et al., "Highly immunogenic and fully synthetic peptide-carrier constructs targeting GnRH," Vaccine, 1999, 17:2043-2050.

(Continued)

*Primary Examiner* — Lauren P Farrar
(74) *Attorney, Agent, or Firm* — Fish & Richardson P.C.

(57) ABSTRACT

This document provides vaccine delivery devices and methods for vaccinating an animal (e.g., a mammal). For example, vaccine delivery devices that include a container having one or more openings, a vaccine depot located within the container, and a diffusion barrier located within the container in a manner such that material (e.g., an antigenic vaccine component) within the vaccine depot must pass through the diffusion barrier before reaching one of the openings are provided.

24 Claims, 6 Drawing Sheets

(56) References Cited

U.S. PATENT DOCUMENTS

| | | | |
|---|---|---|---|
| 2010/0209475 A1* | 8/2010 | Kumar | A61L 27/34 424/426 |
| 2010/0234577 A1* | 9/2010 | Mazzola | C07K 1/18 530/388.1 |
| 2010/0310589 A1* | 12/2010 | Kumar | A61D 1/025 424/184.1 |
| 2011/0028945 A1* | 2/2011 | Amodei | A61K 9/0024 604/890.1 |
| 2015/0246001 A1* | 9/2015 | Zupancich | A61K 9/0024 156/192 |
| 2015/0320938 A1* | 11/2015 | King | A61M 5/31596 604/28 |

OTHER PUBLICATIONS

Mendoza et al., "An in vitro study developing a vaccine delivery device that will maintain life-long titers of anti-GnRH antibodies," Merial-NIH Natinoal Verterinary Scholars Symposium, Jul. 31-Aug. 3, 2014, 1 page.

* cited by examiner

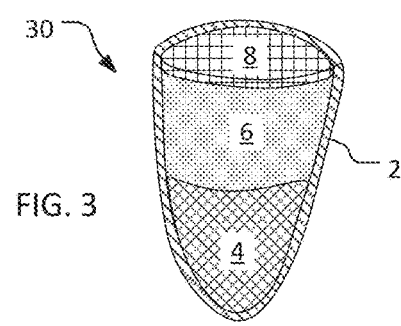

VACCINE DELIVERY DEVICES

CROSS-REFERENCE TO RELATED APPLICATIONS

This application claims the benefit of U.S. Provisional Application Ser. No. 62/121,040, filed Feb. 26, 2015 and U.S. Provisional Application Ser. No. 62/032,475, filed Aug. 1, 2014. The disclosures of the prior applications are considered part of (and are incorporated by reference in) the disclosure of this application.

BACKGROUND

1. Technical Field

This document relates to vaccine delivery devices. For example, this document provides vaccine delivery devices that include a container having one or more openings, a vaccine depot located within the container, and a diffusion barrier located within the container in a manner such that material (e.g., an antigenic vaccine component) within the vaccine depot must pass through the diffusion barrier before reaching one of the openings.

2. Background Information

Vaccines are useful biological preparations designed to induce immune responses with animals. In some case, vaccines can be used to increase a mammal's immunity against pathogens or cancer cells. For example, cancer vaccines can be used to induce a mammal's immune system to target cancer cells. In some cases, vaccines can be used in immunocontraception to induce the immune system of, for example, cats and dogs, to limit reproduction.

SUMMARY

This document provides vaccine delivery devices. For example, this document provides vaccine delivery devices that include a container having one or more openings, a vaccine depot located within the container, and a diffusion barrier located within the container in a manner such that material (e.g., an antigenic vaccine component) within the vaccine depot must pass through the diffusion barrier before reaching one of the openings.

The vaccine delivery devices provided herein can be used to maintain high levels of antibodies (e.g., vaccine-specific or antigen-specific antibodies) for prolonged periods of time following a vaccination (e.g., longer than 1, 2, 3, 4, 5, 6, 7, 8, 9, 10, 11, 12 months or longer than 1, 1.5, 2, 2.5, or 3 years). In some cases, a vaccine delivery device provided herein can maintain high levels of antibodies (e.g., vaccine-specific or antigen-specific antibodies) over the expected lifetime of an animal (e.g., when vaccinating cats, the lifetime of a cat; or when vaccinating dogs, the lifetime of a dog).

As described herein, vaccine delivery devices can be designed to control the release of antigen and/or other vaccine components (e.g., adjuvants) such that antigen is released from the device in an increased amount when antibody levels (e.g., vaccine-specific or antigen-specific antibody levels) within the animal are low and at a decreased level when antibody levels (e.g., vaccine-specific or antigen-specific antibody levels) within the animal are high. In some cases, a vaccine delivery device provided herein can be used as an immunocontraceptive. For example, a gonadotropin-releasing hormone (GnRH)-conjugate can be formulated into a vaccine delivery device provided herein to release the vaccine when it is required to maintain immunity, and little or no vaccine at other times. The use of such a smart stimuli-responsive vaccine release device can maintain high levels of anti-GnRH antibodies over the expected lifetime of the animal, eliminating the need for revaccination and providing for the sustained immunocessation of reproductive behavior and hormonal cycling of, for example, canines and felines.

In general, one aspect of this document provides a vaccine delivery device comprising, or consisting essentially of, (a) a container having a portion of its surface define porous openings that restrict intact cells from passing in and out of the container and that permit antibodies and vaccine antigens to pass in and out of the container, (b) a vaccine depot comprising an antigen and located within the container, and (c) a barrier material located within the container in a position wherein the antigen of the vaccine depot must travel through the barrier material to reach the porous openings, wherein the barrier material allows free antibodies and free antigen to pass through the barrier material, and wherein the barrier material prevents antibody-antigen complexes from passing through the barrier material. The container can comprise a polyvinylidene difluoride membrane defining the porous openings. The porous openings can be about 0.22 μm (or larger up to about 1 μm) in diameter. In some cases, the porous openings can be from about 0.5 μm to about 1 μm (e.g., from about 0.6 μm to about 0.7 μm) in diameter. In some cases, the porous openings can be about 0.66 μm in diameter. In some cases, the membrane defining the porous openings can be asymmetrical with the membrane side closest to the vaccine having openings of about 0.22 μm to about 1 μm, and the side away from the vaccine (in contact with the host) having pore size greater than about 1 μm (e.g., from about 1 μm to about 5 μm) in diameter. In some cases, the vaccine depot can comprise 1,6-bis(p-carboxyphenoxy) hexane (CPH). In some cases, the vaccine depot can comprise polyanhydrides of 1,8-bis(p-carboxyphenoxy)-3,6-dioxaoctane (CPTEG) and CPH. The vaccine depot can comprise CPTEG and CPH in a 50:50 (or 20:80) ratio. The vaccine depot can comprise CPH and sebacic acid (SA). The vaccine depot can comprise CPH and SA in a 20:80 (or 50:50 or 80:20) ratio. The barrier material can comprise collagen. The barrier material can comprise hydroxyapatite. The barrier material can define pores about 20 nm to about 100 nm (e.g., about 40 nm to about 60 nm) or about 20 nm to about 1000 nm (e.g., about 50 nm to about 1000 nm, about 100 nm to about 1000 nm, about 150 nm to about 1000 nm, about 200 nm to about 1000 nm, about 250 nm to about 1000 nm, about 300 nm to about 1000 nm, about 400 nm to about 1000 nm, about 500 nm to about 1000 nm, about 750 nm to about 1000 nm, about 50 nm to about 900 nm, about 50 nm to about 800 nm, about 50 nm to about 700 nm, about 50 nm to about 600 nm, about 50 nm to about 500 nm, about 100 nm to about 500 nm, about 200 nm to about 500 nm, or about 250 nm to about 500 nm) in diameter. In some cases, the barrier material can define pores about 50 nm in diameter.

In another aspect, this document features a method for vaccinating an animal. The method comprises, or consists essentially of, implanting a vaccine delivery device into the animal, wherein the vaccine delivery device comprises, or consists essentially of, (a) a container having a portion of its surface define porous openings, (b) a vaccine depot comprising an antigen and located within the container, and (c) a barrier material located within the container, wherein cells within the animal are restricted from passing into the container, wherein antibodies within the animal are allowed to pass into the container, wherein the antigen of the vaccine depot must travel through the barrier material to reach the porous openings, wherein the barrier material allows free antibodies and free antigen to pass through the barrier material, and wherein the barrier material prevents antibody-antigen complexes from passing through the barrier material. The animal can be a mammal such as a dog, cat, cow, horse, or pig. In some cases, the animal can be a bird such as a chicken or turkey or a fish such as a trout, salmon, or sea bass. The antigen can be gonadotropin-releasing hormone. The container can comprise a polyvinylidene difluoride membrane defining the porous openings. The porous openings can be about 0.22 μm (or larger up to about 1 μm) in diameter. In some cases, the porous openings can be from about 0.5 μm to about 1 μm (e.g., from about 0.6 μm to about 0.7 μm) in diameter. In some cases, the porous openings can be about 0.66 μm in diameter. In some cases, the vaccine depot can comprise CPH. The vaccine depot can comprise CPTEG and CPH. The vaccine depot can comprise CPTEG and CPH in a 50:50 (or 20:80) ratio. The vaccine depot can comprise CPH and SA. The vaccine depot can comprise CPH and SA in a 20:80 (or 50:50 or 80:20) ratio. The barrier material can comprise collagen. The barrier material can comprise hydroxyapatite. The barrier material can define pores about 20 nm to about 100 nm (e.g., about 40 nm to about 60 nm) or about 20 nm to about 1000 nm (e.g., about 50 nm to about 1000 nm, about 100 nm to about 1000 nm, about 150 nm to about 1000 nm, about 200 nm to about 1000 nm, about 250 nm to about 1000 nm, about 300 nm to about 1000 nm, about 400 nm to about 1000 nm, about 500 nm to about 1000 nm, about 750 nm to about 1000 nm, about 50 nm to about 900 nm, about 50 nm to about 800 nm, about 50 nm to about 700 nm, about 50 nm to about 600 nm, about 50 nm to about 500 nm, about 100 nm to about 500 nm, about 200 nm to about 500 nm, or about 250 nm to about 500 nm) in diameter. The barrier material can define pores about 50 nm in diameter.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows a top view of a closed-end container that includes a surface defining opening and that houses a barrier and a vaccine depot, in accordance with some embodiments.

FIG. 1B shows a side cross-sectional view of the container of FIG. 1A.

FIG. 1C shows a bottom view of the container of FIG. 1A.

FIG. 2A shows a top view of a tube-like container that includes two surfaces defining openings and that houses a first barrier, a vaccine depot, and a second barrier, in accordance with some embodiments.

FIG. 2B shows a side cross-sectional view of the container of FIG. 2A.

FIG. 2C shows a bottom view of the container of FIG. 2A.

FIG. 3 shows a cross-sectional view of a container that includes a surface defining opening and that houses a barrier and a vaccine depot, in accordance with some embodiments.

Like reference symbols in the various drawings indicate like elements.

DETAILED DESCRIPTION

Figure 4:
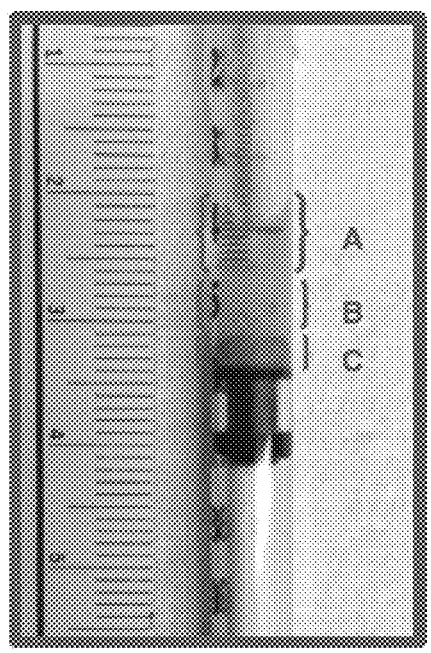
FIG. 4 is a photograph of a control device having layer A with purified rabbit IgG antibodies in PBS, layer B with a collagen hydrogel layer, and layer C with a polyanhydride blended with fluorescently labeled Ova.
Figure 5:
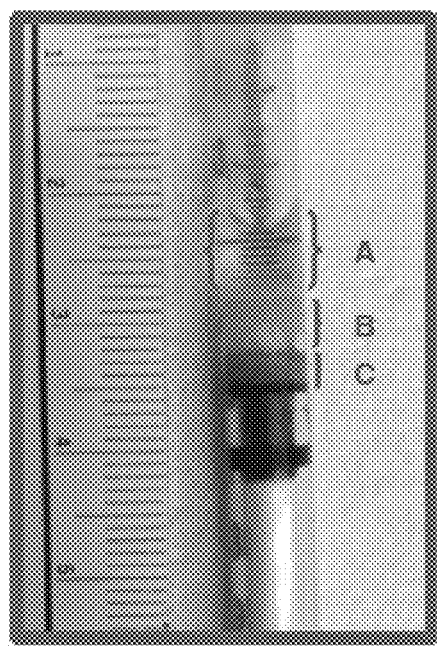
FIG. 5 is a photograph of a sample device having layer A with anti-Ova antibodies in PBS, layer B with a collagen hydrogel layer, and layer C with a polyanhydride blended with fluorescently labeled Ova.
Figure 6:
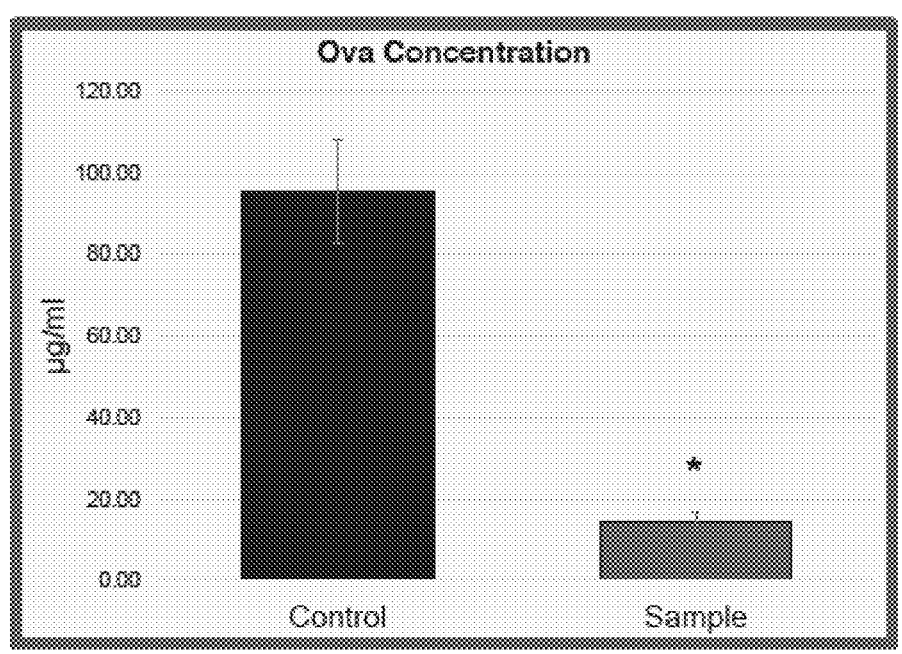
FIG. 6 is a graph plotting Ova concentration. Fluorescently labeled Ova was measured in supernatants of each device (n=3 experiments with 3 replicates per experiment; expressed as average +/−SEM). A significant difference was found between the control group versus sample group. $*p \leq 0.05$.
Figure 7:
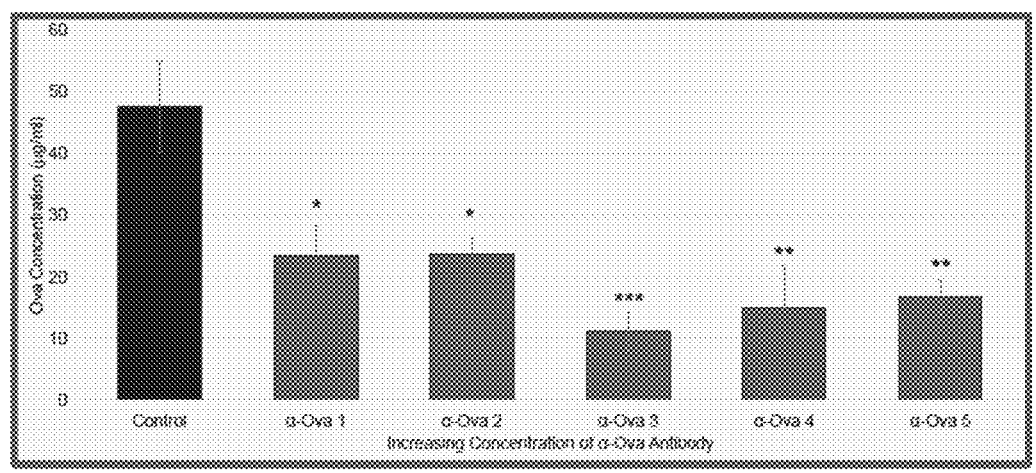
FIG. 7 is a graph plotting dose response results from in vitro devices, which reveal significant differences between the control group versus sample groups at differing increasing concentrations of anti-Ova antibody after five days (n=4; expressed as average +/−SEM). $*p \leq 0.05$, $p \leq 0.01$, $*p \leq 0.001$.
Figure 8A:
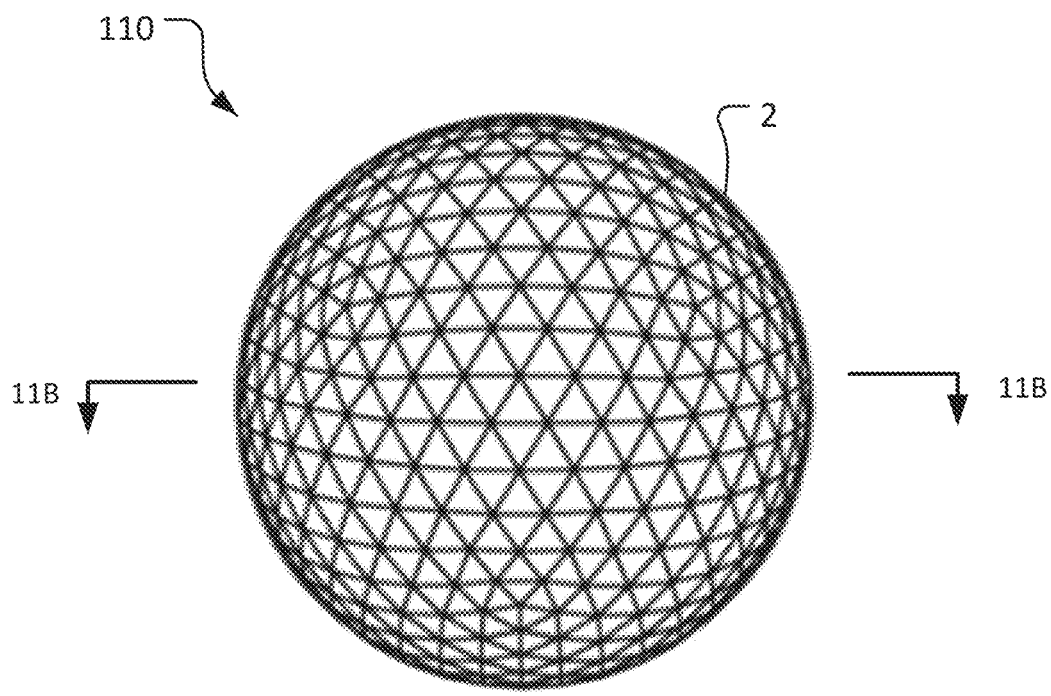
FIG. 8A shows a side view of a container that has a surface defining openings and that houses a barrier and a vaccine depot, in accordance with some embodiments.
Figure 8B:
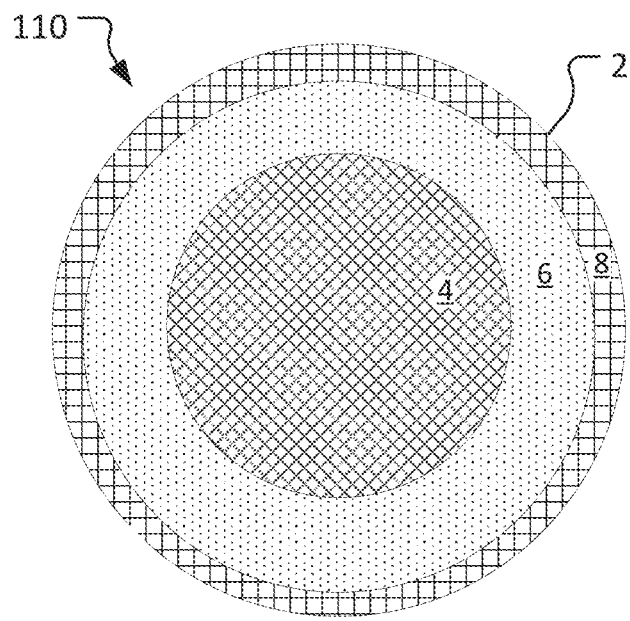
FIG. 8B shows a top cross-sectional view of the container of FIG. 8A.

This document provides vaccine delivery devices and methods for vaccinating a mammal (e.g., a dog, cat, horse, sheep, pig, cow, heifer, calf, bull, steer, goat, llama, ferret, or humans), a bird (e.g., a chicken and turkey) and fish (e.g., a trout, salmon, or sea bass) using a vaccine delivery device provided herein. For example, this document provides vaccine delivery devices that include a container having one or more openings, a vaccine depot located within the container, and a diffusion barrier located within the container in a manner such that material (e.g., an antigenic vaccine component) within the vaccine depot must pass through the diffusion barrier before reaching one of the openings.

The container of a vaccine delivery device provided herein can be any appropriate shape and size. For example, a container of a vaccine delivery device provided herein can be rectangular, cylindrical, spherical, a cone, or a disk. In some cases, when rectangular, the container can have a length of between about 10 mm and about 25 mm, a width of between about 3 mm and about 5 mm, and a height of between about 3 mm and about 5 mm. When cylindrical, the container can have a length of between about 10 mm and about 25 mm and a diameter of between about 3 mm and about 7 mm. When spherical, the container can have a diameter of between about 3 mm and about 7 mm. In addition, the walls of a container of a vaccine delivery device provided herein can be any appropriate thickness. For example, the walls of a container of a vaccine delivery device provided herein can be between about 100 nm and about 2 mm in thickness. In some cases, the thickness of the walls of a container can be constant throughout the container or can be variable with some sections being thicker than others.

Any appropriate material can be used to make a container of a vaccine delivery device provided herein. For example, polyethylene, polypropylene, polycarbonate, polyvinylfluoride, polysulfones, silicone polymers, polyamides, cellulose, polyglycols, polyfluoroolefins, and combinations thereof can be used to make a container of a vaccine delivery device provided herein. In some cases, one or more biodegradable material can be used to make a container of a vaccine delivery device provided herein. Examples of biodegradable materials that can be used to make a container of a vaccine delivery device provided herein include, without limitation, polyesters such as poly(lactic acid) poly(glycolic acid), and copolymers thereof, poly(ε-caprolactone), chitosan, polyanhydride, polyester/polyamide, polyvinyl alcohol, polyvinyl pyrrolidone, and combinations thereof. In some cases, one or more biodegradable materials can be used to make a container of a vaccine delivery device provided herein such that the container completely degrades within an animal (e.g., a mammal) only after being present within the animal (e.g., mammal) for at least 1 year. For example, materials such as polyanhydride, cellulose, polyglycols, and combinations thereof can be used to construct a container of a vaccine delivery device provided herein such that the container completely degrades within an animal (e.g., a mammal) only after being present within the animal (e.g., mammal) for at least 1 year.

The container of a vaccine delivery device provided herein can include one or more (e.g., one, two, three, four, five, six, seven, eight, nine, ten, or more) openings. In general, these openings are configured to have a shape or size (e.g., a diameter) that restricts intact cells (e.g., immune cells such as B-cells, T-cells, macrophages, dendritic cells, or neutrophils) from passing in and out of the container, while permitting antibodies and/or vaccine antigens to pass in and out of the container. For example, the openings can have a minimum diameter of about 50 nm and a maximum diameter of about 6 μm. In some cases, the openings of a container of a vaccine delivery device provided herein can be between about 50 nm and about 3 μm (e.g., between about 50 nm and about 6 μm, between about 75 nm and about 6 μm, between about 100 nm and about 6 μm, between about 100 nm and about 3 μm, between about 250 nm and about 3 μm, between about 500 nm and about 3 μm, between about 1 μm and about 3 μm, between about 50 nm and about 3 μm, between about 50 nm and about 2 μm, between about 50 nm and about 1 μm, between about 50 nm and about 0.75 μm, between about 50 nm and about 0.5 μm, between about 50 nm and about 0.25 μm, between about 75 nm and about 3 μm, between about 100 nm and about 2.5 μm, between about 250 nm and about 2 μm, or between about 500 nm and about 1 μm).

In some cases, one or more portions of the container or the entire container can be constructed with porous material to provide these openings. For example, one or both ends of a cylindrical container can be constructed with porous material having average pore sizes between about 50 nm and about 6 μm (e.g., between about 50 nm and about 6 μm, between about 75 nm and about 6 μm, between about 100 nm and about 6 μm, between about 100 nm and about 3 μm, between about 250 nm and about 3 μm, between about 500 nm and about 3 μm, between about 1 μm and about 3 μm, between about 50 nm and about 3 μm, between about 50 nm and about 2 μm, between about 50 nm and about 1 μm, between about 50 nm and about 0.75 μm, between about 50 nm and about 0.5 μm, between about 50 nm and about 0.25 μm, between about 75 nm and about 3 μm, between about 100 nm and about 2.5 μm, between about 250 nm and about 2 μm, or between about 500 nm and about 1 μm). In one example, a spherical container can be designed entirely with porous material such that all the pores are between about 50 nm and about 6 μm (e.g., between about 50 nm and about 6 μm, between about 75 nm and about 6 μm, between about 100 nm and about 6 μm, between about 100 nm and about 3 μm, between about 250 nm and about 3 μm, between about 500 nm and about 3 μm, between about 1 μm and about 3 μm, between about 50 nm and about 3 μm, between about 50 nm and about 2 μm, between about 50 nm and about 1 μm, between about 50 nm and about 0.75 μm, between about 50 nm and about 0.5 μm, between about 50 nm and about 0.25 μm, between about 75 nm and about 3 μm, between about 100 nm and about 2.5 μm, between about 250 nm and about 2 μm, or between about 500 nm and about 1 μm) in diameter.

Examples of porous material that can be used to construct one or more portions of the container or the entire container include, without limitation, polyvinylidene difluoride membrane material, polyethersulfone, polycarbonate, polytetrafluoroolefins, polypropylene, polyethylene, and polysulfone.

As described herein, the container of a vaccine delivery device provided herein can house one or more vaccine depots and barrier material. In general, a vaccine depot includes one or more immunogens for vaccinating a mammal (e.g., a dog, cat, horse, sheep, pig, cow, heifer, calf, steer, bull, goat, llama, ferret, or human), a bird (e.g., a chicken and turkey), or a fish (e.g., a trout, salmon, or sea bass). For example, a vaccine depot can include the immunogen or immunogens or vaccine antigen or antigens of an anti-pathogen vaccine, an anti-cancer vaccine, or an immunocontraception vaccine. Examples of immunogens of an anti-pathogen vaccine that can be formulated into a vaccine depot and used as described herein include, without limitation, antigens (e.g., hemagglutinin, neuraminidases, glycoproteins, or nucleoproteins) from viruses such as dengue, HIV, feline panleukopenia virus, feline infectious peritonitis virus, rabies, porcine reproductive and respiratory disease virus (PRRS), bursal disease virus, caprine arthritis and encephalitis virus, and hepatitis virus, antigens (e.g., F1-V, PspA, rPA) from bacteria such as *Mycobacterium tuberculosis, Clostridium tetani* (e.g., tetanus), *Mycobacterium avium* paratuberculosis, *Anaplasma, Borrelia, Leptospira, Ehrlichia, Brucella, Vibrio*, and *Aeromonas*, antigens from fungal organism such as *Cryptococcus, Histoplasma, Pneumocystis*, and *Aspergillus*, antigens from protozoans such as *Plasmodium* (malaria), *Leishmania, Babesia, Eimeria*, and *Icthyopthiris multifiliis*, and antigens from nematodes such as *Ascaris, Ancyclostoma, Necator, Oesophagostomum*, and *Haemonchus*. Examples of immunogens of an anti-cancer vaccine that can be formulated into a vaccine depot and used as described herein include, without limitation, cancer antigens such as MUC-1, CA-125, Prostate serum antigen, and mesothelin. Examples of immunogens of an immunocontraception vaccine that can be formulated into a vaccine depot and used as described herein include, without limitation, antigens such as gonadotropin-releasing hormone, gonadotropin-releasing hormone linked to carrier proteins such as the mollusk hemocyanins blue protein, keyhole limpet hemocyanian, or ovalbumin, luteinizing hormone, luteinizing hormone beta subunit, and porcine zona pellucida. In some cases, a vaccine depot can include a multiple antigenic peptide of GnRH dimer as described elsewhere (Beekman et al., *Vaccine,* 17:2043-2050 (1999)).

A vaccine depot can include any appropriate amount of an immunogen. For example, a vaccine depot can be formulated to include between about 500 ng and about 1 mg by weight of an immunogen of, for example, about 10,000 and 100,000 MW (e.g., about 18,000 MW).

In some cases, a vaccine depot housed within a container of a vaccine delivery device provided herein can include one or more additional components. For example, a vaccine depot can be formulated to include one or more polyanhydride materials. Examples of polyanhydride materials include, without limitation, materials based on monomers such as 1,8-bis(p-carboxyphenoxy)-3,6-dioxaoctane (CPTEG), 1,6-bis(p-carboxyphenoxy) hexane (CPH), sebacic acid (SA), 1,3-bis(p-carboxyphenoxy)propane (CPP), and fumaric acid (FA). In some cases, mixtures of different polyanhydride materials of various copolymer compositions can be included as part of a vaccine depot. For example, a mixture having between about 10:90 of CPTEG to CPH to about 90:10 of CPTEG to CPH can be included within a vaccine depot. In some cases, a vaccine depot can include a mixture having about 20:80 of CPTEG to CPH. In some cases, a mixture having between about 0:100 of CPH to SA to about 100:0 of CPH to SA can be included within a vaccine depot. In some cases, a vaccine depot can include a mixture having about 80:20 of CPH to SA.

In some cases, a vaccine depot can include one or more inhibitors of complement activation. Examples of inhibitors of complement activation that can be formulated into a vaccine depot that is housed within a container of a vaccine delivery device provided herein include, without limitation, C1-inhibitors, protectin (CD59), decay accelerating factor (DAF), Factor H, Serping 1, and sialylation of the polyanhydride with n-acetylneuraminic acid. A vaccine depot can include any appropriate amount of an inhibitor of complement activation. For example, a vaccine depot can be formulated to include between about 0.001 µM and about 1000 µM of an inhibitor of complement activation.

In some cases, a vaccine depot can include one or more protease inhibitors. Examples of protease inhibitors that can be formulated into a vaccine depot that is housed within a container of a vaccine delivery device provided herein include, without limitation, tissue inhibitors of metalloproteinase (TIMP) 1, 2, 3, and 4 and commercial broad spectrum metalloproteinase inhibitors such as CP-471474, PGE-530742, and PD166793. A vaccine depot can include any appropriate amount of a protease inhibitor. For example, a vaccine depot can be formulated to include between about 1 µg (or 3 nM) and about 1000 µg (or about 3 µM) of a protease inhibitor.

In some cases, a vaccine depot can include one or more adjuvants. Examples of adjuvants that can be formulated into a vaccine depot that is housed within a container of a vaccine delivery device provided herein include, without limitation, Aluminum hydroxide, monophosphoryl lipid A, CpG oligonucleotides, and saponin. A vaccine depot can include any appropriate amount of an adjuvant. For example, a vaccine depot can be formulated to include between about 1 µg (or about 500 µM) and about 100 µg (or about 50 mM) of an adjuvant such as monophosphoryl lipid A.

In some cases, a vaccine depot can include one or more chemokines. Examples of chemokines that can be formulated into a vaccine depot that is housed within a container of a vaccine delivery device provided herein include, without limitation, CCL2, CCL3, CCL5, CCL8, CXCL13, CCL17, and CCL22. A vaccine depot can include any appropriate amount of CCL2. For example, a vaccine depot can be formulated to include between about 1 ng (or about 1 nM) and about 1 mg (or about 1 mM) of CCL2.

In some cases, a vaccine depot can include one or more cytokines. Examples of cytokines that can be formulated into a vaccine depot that is housed within a container of a vaccine delivery device provided herein include, without limitation, Interleukin 2, Interferon gamma, Interleukin-12p70, tumor necrosis factor-$\alpha$, Interleukin 4, granulocyte colony stimulating factor, Interleukin 10, and granulocyte/macrophage colony stimulating factor. A vaccine depot can include any appropriate amount of granulocyte/macrophage colony stimulating factor. For example, a vaccine depot can be formulated to include between about 1 ng (or about 0.5 nM) and about 100 µg (or about 50 µM) of granulocyte/macrophage colony stimulating factor.

As described herein, the container of a vaccine delivery device provided herein can be configured to house at least one vaccine depot and barrier material in an arrangement where the immunogens of the vaccine depot must travel through at least a portion of the barrier material before reaching an opening of the container. For example, when an entire spherical container is constructed of porous material, then the vaccine depot can be configured as a core completely surrounded by a mantel of barrier material. In this case, the immunogens or antigens of the vaccine depot must travel through the barrier material before being able to exit the container through the pores of the porous material.

As described herein, the barrier material can be constructed to allow free antibodies and free antigen (e.g., the immunogens of the vaccine depot) to pass through the barrier material, while preventing antibody-antigen complexes from passing through the barrier material. Examples of materials that can be used to make a barrier material of a vaccine delivery device provided herein include, without limitation, cross-linked Type 1 collagen, cross-linked Type II collagen, hydroxyapatite, cross-linked polyvinyl alcohol, cross-linked polyvinyl pyrrolidone, and cross-linked polyvinyl acrylamide, polyhydroxyethylmethacrylate, silica gels, maleic anhydride co-polymers, and pluronic.

In some cases, a diffusion assay can be performed to confirm that a particular formulation of material has the ability to be a barrier material that allows free antibodies and free antigen to pass through the barrier material, while preventing antibody-antigen complexes from passing through the barrier material. For example, labeled antibodies alone or labeled antigens alone can be monitored to determine if they pass through the barrier material being tested. If the labeled antibodies or labeled antigens pass through the barrier material being tested, then labeled antibody-antigen complexes can be monitored to determine if the complexes are restricted from passing through the material. If the complexes are restricted from passing through the material and the free antibodies and free antigens are not restricted from passing through the material, then that material or arrangement of material can be used as a barrier material within a container as described herein.

In some cases, the barrier material of a vaccine delivery device provided herein can be replaced with a movement limiting material that allows free antibodies and free antigen to pass through the movement limiting material at free-antibody rate and at a free-antigen rate, respectively, and that allows antibody-antigen complexes to pass through the movement limiting material at an antibody-antigen complex rate. In these cases, the antibody-antigen complex rate can be slower than the free-antibody rate and the free-antigen rate. In some cases, the antibody-antigen complex rate can be at least two, three, four, five, six, seven, eight, nine, ten, or more times slower than the free-antibody rate or the free-antigen rate. For example, the antibody-antigen complex rate can be at least 10, 25, 50, 100, 250, 500, 750, or 1000 times slower than the free-antibody rate or the free-antigen rate. Examples of materials that can be used to make a movement limiting material of a vaccine delivery device provided herein include, without limitation, cross-linked polyacrylamide, agarose, collagen gelatin, and gel forming polysaccharides, silica gels, agar, polyhydroxyethylmethacrylate, and pluronic-based composite forming gels.

In some cases, the barrier material of a vaccine delivery device provided herein can be replaced with a movement limiting material that allows free antibodies and free antigen to pass through the movement limiting material at free-antibody rate and at a free-antigen rate, respectively, and that allows antibody-antigen complexes to pass through the movement limiting material at an antibody-antigen complex rate. In these cases, the antibody-antigen complex rate can be slower than the free-antibody rate and the free-antigen rate. In some cases, the antibody-antigen complex rate can be at least two, three, four, five, six, seven, eight, nine, ten, or more times slower than the free-antibody rate or the free-antigen rate. For example, the antibody-antigen complex rate can be at least 10, 25, 50, 100, 250, 500, 750, or 1000 times slower than the free-antibody rate or the free-antigen rate. Examples of materials that can be used to make a movement limiting material of a vaccine delivery device provided herein include, without limitation, asymmetric porous membranes and hydroxyapatite-based nanocomposites.

In some cases, a container of a vaccine delivery device provided herein can include both barrier material and movement limiting material. For example, a container can house a vaccine depot surrounded by a layer of movement limiting material that is surrounded by a layer of barrier material. As another example, a container can house a vaccine depot surrounded by a layer of movement limiting material, which can be surrounded by a layer of barrier material, which can be surrounded by a layer of movement limiting material.

In some cases, at least a portion of the barrier material, movement limiting material, or both can include one or more inhibitors of complement activation and/or one or more protease inhibitors. In some cases, at least a portion of the barrier material, movement limiting material, or both can include one or more inhibitors of complement activation and/or one or more protease inhibitors that are cross-linked to the barrier material or movement limiting material. For example, barrier material that includes collagen and/or hydroxyapatite can include one or more inhibitors of complement activation and/or one or more protease inhibitors crosslinked to the collagen and/or hydroxyapatite. These inhibitors can help reduce the clearance of vaccine components from within the vaccine delivery device by complement or protease processes. In some cases, a vaccine deliver device can house one or more inhibitors of complement activation and/or one or more protease inhibitors that are linked to large molecules that are prevented from traveling through the barrier material, and are therefore retained within the vaccine delivery device.

Any appropriate method can be used to make barrier material or movement limiting material for a vaccine delivery device provided herein. For example, disk or cylinder-shaped nanocomposites of desired dimensions can be pressed at pressure of 3 metric tons for 2 minutes using a hydraulic Carver Press (Wabash, Ind., USA).

Referring to FIGS. 1A-1C, a vaccine delivery device 10 includes a closed-end cylindrical container 2 with a surface defining openings 8. Openings 8 can be configured as described herein to have a shape or size (e.g., a diameter) that restricts intact cells (e.g., immune cells such as B-cells, T-cells, macrophages, or neutrophils) from passing in and out of container 2, while permitting antibodies and/or vaccine antigens to pass in and out of container 2. Container 2 can house a barrier 6 and a vaccine depot 4. Vaccine depot 4 can be composed of one or more components as described herein. In addition, vaccine depot 4 can be disposed adjacent to the closed-end of container 2. Openings 8 can be located at another end of container 2. Barrier 6 can be constructed to allow free antibodies and free antigen (e.g., immunogens of vaccine depot 4) to pass through barrier 6, while preventing antibody-antigen complexes from passing through barrier 6. In addition, barrier 6 can be in an arrangement where the immunogens of vaccine depot 4 must travel through at least a portion of barrier 6 before reaching openings 8 of container 2. For example, barrier 6 can be disposed between openings 8 and vaccine depot 4.

Referring to FIGS. 2A-2C, a vaccine delivery device 20 includes a tube-like cylindrical container 2 with a first surface defining openings **8*a* and a second surface defining openings 8*b*. Container 2 can house a first barrier 6*a*, a vaccine depot 4, and a second barrier 6*b*. First barrier 6*a* can be disposed adjacent to openings 8*a*. Second barrier 6*b* can be disposed adjacent to openings 8*b*. Vaccine depot 4 can be disposed between first barrier 6*a* and second barrier 6*b***.

Referring to FIG. 3, a vaccine delivery device 30 can include a vial-like container 2 with a top portion that defines openings 8. Container 2 can house a barrier 6 and vaccine depot 4. Vaccine depot 4 can be disposed adjacent to the closed-end of container 2. Barrier 6 can be disposed between openings 8 and vaccine depot 4.

Referring to FIGS. 8A and 8B, a vaccine delivery device 110 can include a spherical container 2 that defines openings 8. Container 2 can house a barrier 6 that surrounds a vaccine depot 4. Vaccine depot 4 can be configured as a core within container 2.

The invention will be further described in the following examples, which do not limit the scope of the invention described in the claims.

EXAMPLES

Example 1

A Vaccine Delivery Device that Maintains Titers of Anti-GnRH Antibodies

Overpopulation is an ongoing problem for dogs and cats throughout the United States. In 2012-2013, the Humane Society of the United States estimated that there were about 6 to 8 million cats and dogs entering animal shelters. Of that amount, approximately 2.7 million adoptable dogs and cats were euthanized. To combat pet overpopulation, shelters across the nation advocate for spaying and neutering of pets to prevent unwanted pregnancies and unnecessary euthanasia.

Surgical intervention is the most common form of sterilization of dogs and cats to date, with several chemical contraceptive methods as minor forms. The idea of immunocontraception, using the immune system to limit reproduction, has been used in wildlife populations with some important successes. However, it has been a challenge to create a long term and cost-effective method of non-surgical contraception. Development of a successful, single shot vaccine as a form of sterilization technique that can maintain life-long titers of antibodies targeting the central regulator of reproductive hormones, gonadotropin releasing hormone (GnRH), may be a potential solution to this problem. One goal is to develop an implantable vaccine device that takes advantage of the animal's own immune response to regulate release of the vaccine eliminating the need for boosters and enabling multi-year immunity with a single implant. An in vitro system was assembled that releases a model antigen, ovalbumin (Ova), from a prototype of the vaccine device using different types of polymers. A tiered polymer-hydrogel design can be used to control release of antigen in an antibody dependent manner.

Polyanhydride Preparation for In Vitro Device

PA polymer and Ova mixture was prepared by dissolving 0.7% w/w fluorescent Ova (Molecular Probes) to PA in dichloromethane (Sigma Aldrich). The mixture was vortexed for 30 seconds and sonicated with a probe sonicator for 10 to 15 seconds until uniform. The mixture was transferred into a Span-80 (Sigma Aldrich) coated 1 CC syringe (BD). The PA and fluorescent Ova blend was dried for two days under the hood at room temperature. After drying, the PA was rinsed with PBS one time, and a sterile collagen hydrogel was added on top. 100 μL of 0.5% type I collagen was added under sterile conditions. The top of the syringe was covered loosely with parafilm, and it was placed in 37° C. incubator for 1 hour.

The type I collagen was cross-linked as follows. 100 μL of 5 mg/mL EDC (1-Ethyl-3 (3-dimethylaminopropyl)carbodiimide hydrochloride) was added to the syringe on top of the collagen. The syringe with PA, collagen, and EDC was placed in a 37° C. incubator for 3 hours. The EDC was removed, and the material was rinsed two times with PBS. The PBS was removed leaving the PA and cross-linked collagen barrier.

In Vitro Device Conditions

100 μL of 5 mg/mL purified rabbit IgG (Invitrogen) antibodies were added on top of the control devices. 100 μL of 5 mg/mL purified rabbit anti-Ova antibodies (Millipore; Cat. No. AB1225) were added to the sample devices. Fluorescently labeled Ova was measured on a Molecular Devices plate reader at excitation 652 nm and emission 668 nm after five days.

Antibody Dose Response

PA and in vitro devices were prepared using the same protocol in addition to five different, decreasing concentrations of anti-Ova (1-5) antibodies with purified rabbit IgG antibodies as a control. Fluorescent readings were measured after five days for FIG. 7.

Statistical Analysis

Analysis on in vitro devices performed T-test on Microsoft Excel or One-way ANOVA with Tukey's multiple comparisons test on Graph Pad Prism Software.

Results

The results are shown in FIGS. 4-7.

Tiered PA and Hydrogel Device

PA in combination with a hydrogel was used in the in vitro delivery device system. When fluorescence was measured, there was significantly more Ova in the supernatant of the control device than that of the sample device, which contained anti-Ova antibodies. Ova in the control device freely moved out of the PA/hydrogel system in the presence of non-specific IgG, while the Ova was trapped by immune complexes formed in the presence of anti-Ova antibodies within the sample device. Visual evidence was presented in FIGS. 4 and 5.

Anti-Ova Antibody Dose Response

A dose response experiment was performed to determine the concentration of antibodies that have the most effect on Ova being released from the PA and hydrogel blend. The same effect as shown FIGS. 4 and 6 was replicated at differing levels. With the addition of increasing concentration of anti-Ova antibodies, an inverse bell shaped pattern was formed. This can be described by the antibody-antigen equivalence phenomenon, where antibody or antigen excess insufficiently produce immune complexes, but at equivalent concentrations of both antibody and antigen, immune complex formation is optimized. The latter is shown at anti-Ova dose #3 (FIG. 7).

The results provided herein demonstrate that a vaccine delivery device can be made up of PA and hydrogel to successfully slow the release of a model antigen (Ova) in the presence of anti-Ova antibodies. This release also is able to be controlled based on the amount of anti-Ova antibody present. These results also demonstrate that it is possible to formulate a vaccine that sustains release of its antigen in order to maintain life-long titers of antibodies.

Example 2

A Vaccine Delivery Device that Maintains Titers of Anti-GnRH Antibodies and Provides Immunocontraception in Dogs A high molecular weight polyethylene implant of 20 mm long and 6.35 mm outside diameter and internal diameter of 4 mm with a total volume of 225 microliters capped with 0.66 micron pore PVDF membrane is used. 138 mg (125 μL) of a solid solution of 20% CPTEG (poly1,8-bis[p-carboxyphenoxy]3,6-dioxaoctane) and 80% CPH (1,6-bis[p-carboxyphenoxy]hexane), polyCPTEG-CPH (20:80), with 0.65% weight (0.9 mg) of a vaccine antigen consisting of a synthesized GnRH-multiple antigenic peptide (GnRH-MAP) with between 70-80% of the GnRH-MAP conjugated to a 4 arm polyethylene glycol dendrimer (GnRH-MAP-PEG) to increase the molecular weight of the vaccine antigen and increase antibody binding sites. The GnRH-MAP is synthesized using conventional Fmoc chemistry by a commercial source (e.g., Bio-Synthesis, Lewisville Tex.). The peptides are synthesized on a lysine core resin with 8 terminal branches bearing a GnRH dimer peptide with the sequence: Pyr-HWSYGLRPGQHWSY-GLRPG-Lys where Pyr-H is a pyroglutamic acid. As needed the MAP peptide will be synthesized by the commercial source (Biosyn) with a thiol group (cystamide) at the C-terminus of the free alanine and conjugated to a 4-arm poly-ethylene glycol dendrimer (PEG40K) maleimide. After conjugation, the conjugate will be dialyzed in PBS to decrease the amount of free MAP peptide that is not conjugated to the PEG. After this process 70-80% of the GnRH-MAP is conjugated to the PEG (GnRH-MAP PEG) 20-30% of the final product is free GnRH-MAP. The following is placed on top of this solid solution: a diffusion barrier of 100 microliters of 0.5% type I collagen, which is allowed to polymerize at 37° C. for 1 hour. The diffusion barrier is cross-linked with EDC for 3 hours at 37° C. and then rinsed three times with PBS. The implant cap with a PVDF membrane with 0.66 micron pores is affixed to the implant with methacrylate adhesive. The implant is placed into the subcutaneous tissue of the dog in conjunction with 500 microliters of a soluble GnRH vaccine consisting of the 300 μg GnRH-MAP construct linked to Blue Protein carrier protein from a commercial supplier (e.g., Pearce) in alum adjuvant (50:50 by volume), as well as a 208 mg by weight slow release polyanhydride tablet of 10 mm in length and 4 mm in diameter consisting of a solid solution of polyCPTEG-polyCPH (20:80) and 0.14% GnRH-MAP (300 µg) and 0.05% MPLA adjuvant (100 µg) by weight.

Example 3

A Vaccine Delivery Device that Maintains Titers of Anti-GnRH Antibodies and Provides Immunocontraception in Cats A high molecular weight polyethylene implant of 20 mm long and 6.35 mm outside diameter and internal diameter of 4 mm with a total volume of 225 microliters capped with 0.66 micron pore PVDF membrane is used. 138 mg (125 µL) of a solid solution of 20% CPTEG (poly1,8-bis[p-carboxyphenoxy]3,6-dioxaoctane) and 80% CPH (1,6-bis[p-carboxyphenoxy]hexane), polyCPTEG-CPH (20:80), with 0.65% weight (0.9 mg) of a vaccine antigen consisting of a synthesized GnRH-multiple antigenic peptide (GnRH-MAP) with between 70-80% of the GnRH-MAP conjugated to a 4 arm polyethylene glycol dendrimer (GnRH-MAP-PEG) to increase the molecular weight of the vaccine antigen and increase antibody binding sites. The GnRH-MAP is synthesized using conventional Fmoc chemistry by a commercial source (e.g., Bio-Synthesis, Lewisville Tex.). The peptides are synthesized on a lysine core resin with 8 terminal branches bearing a GnRH dimer peptide with the sequence: Pyr-HWSYGLRPGQHWSY-GLRPG-Lys where Pyr-H is a pyroglutamic acid. As needed the MAP peptide will be synthesized by the commercial source (Biosyn) with a thiol group (cystamide) at the C-terminus of the free alanine and conjugated to a 4-arm poly-ethylene glycol dendrimer (PEG40K) maleimide. After conjugation, the conjugate will be dialyzed in PBS to decrease the amount of free MAP peptide that is not conjugated to the PEG. After this process 70-80% of the GnRH-MAP is conjugated to the PEG (GnRH-MAP PEG) 20-30% of the final product is free GnRH-MAP. The following is placed on top of this solid solution: a diffusion barrier of 100 microliters of 0.5% type I collagen, which is allowed to polymerize at 37° C. for 1 hour. The diffusion barrier is cross-linked with EDC for 3 hours at 37° C. and then rinsed three times with PBS. The implant cap with a PVDF membrane with 0.66 micron pores is affixed to the implant with methacrylate adhesive. The implant is placed into the subcutaneous tissue of the cat in conjunction with 500 microliters of a soluble GnRH vaccine consisting of the 300 µg GnRH-MAP construct linked to Blue Protein carrier protein from a commercial supplier (e.g., Pearce) in alum adjuvant (50:50 by volume), as well as a 208 mg by weight slow release polyanhydride tablet of 10 mm in length and 4 mm in diameter consisting of a solid solution of polyCPTEG-polyCPH (20:80) and 0.14% GnRH-MAP (300 µg) and 0.05% MPLA adjuvant (100 µg) by weight.

Example 4

A Vaccine Delivery Device that Maintains Titers of Anti-GnRH Antibodies and Provides Immunocontraception in Horses A high molecular weight polyethylene implant of 20 mm long and 6.35 mm outside diameter and internal diameter of 4 mm with a total volume of 225 microliters capped with 0.66 micron pore PVDF membrane is used. 138 mg (125 µL) of a solid solution of 20% CPTEG (poly1,8-bis[p-carboxyphenoxy]3,6-dioxaoctane) and 80% CPH (1,6-bis[p-carboxyphenoxy]hexane), polyCPTEG-CPH (20:80), with 0.65% weight (0.9 mg) of a vaccine antigen consisting of a synthesized GnRH-multiple antigenic peptide (GnRH-MAP) with between 70-80% of the GnRH-MAP conjugated to a 4 arm polyethylene glycol dendrimer (GnRH-MAP-PEG) to increase the molecular weight of the vaccine antigen and increase antibody binding sites. The GnRH-MAP is synthesized using conventional Fmoc chemistry by a commercial source (e.g., Bio-Synthesis, Lewisville Tex.). The peptides are synthesized on a lysine core resin with 8 terminal branches bearing a GnRH dimer peptide with the sequence: Pyr-HWSYGLRPGQHWSY-GLRPG-Lys where Pyr-H is a pyroglutamic acid. As needed the MAP peptide will be synthesized by the commercial source (Biosyn) with a thiol group (cystamide) at the C-terminus of the free alanine and conjugated to a 4-arm poly-ethylene glycol dendrimer (PEG40K) maleimide. After conjugation, the conjugate will be dialyzed in PBS to decrease the amount of free MAP peptide that is not conjugated to the PEG. After this process 70-80% of the GnRH-MAP is conjugated to the PEG (GnRH-MAP PEG) 20-30% of the final product is free GnRH-MAP. The following is placed on top of this solid solution: a diffusion barrier of 100 microliters of 0.5% type I collagen, which is allowed to polymerize at 37° C. for 1 hour. The diffusion barrier is cross-linked with EDC for 3 hours at 37° C. and then rinsed three times with PBS. The implant cap with a PVDF membrane with 0.66 micron pores is affixed to the implant with methacrylate adhesive. The implant is placed into the subcutaneous tissue of the horse in conjunction with 500 microliters of a soluble GnRH vaccine consisting of the 300 µg GnRH-MAP construct linked to Blue Protein carrier protein from a commercial supplier (e.g., Pearce) in alum adjuvant (50:50 by volume), as well as a 208 mg by weight slow release polyanhydride tablet of 10 mm in length and 4 mm in diameter consisting of a solid solution of polyCPTEG-polyCPH (20:80) and 0.14% GnRH-MAP (300 µg) and 0.05% MPLA adjuvant (100 µg) by weight.

Example 5

A Vaccine Delivery Device that Maintains Titers of Anti-Bovine Herpes Virus-1 Antibodies and Provides Long Term Protection Against Infectious Bovine Rhinotracheitis (IBR)

A high molecular weight polyethylene implant of 20 mm long and 6.35 mm outside diameter and internal diameter of 4 mm with a total volume of 225 microliters capped with 0.66 micron pore PVDF membrane is used. 110 mg (100 µL) of a solid solution of 20% CPTEG (poly1,8-bis[p-carboxyphenoxy]3,6-dioxaoctane) and 80% CPH (1,6-bis[p-carboxyphenoxy]hexane) is placed with 0.45% weight (500 µg) of vaccine antigen consisting of a whole killed Bovine herpesvirus-1. The following is placed on top of this solid solution: a diffusion barrier of 100 microliters of 0.5% type I collagen, which is allowed to polymerize at 37° C. for 1 hour. The diffusion barrier is cross-linked with EDC for three hours at 37° C. and then rinsed three times with PBS. The implant cap with a PVDF membrane with 0.66 micron pores is affixed to the implant with methacrylate adhesive. The implant is placed into the subcutaneous tissue of the bovine in conjunction with 500 microliters of a soluble whole killed bovine herpes virus-1 vaccine consisting of the 40 µg of whole killed bovine herpes virus-1 in alum adjuvant (50:50 by volume), as well as a 208 mg slow release polyanhydride tablet of 10 mm in length and 4 mm in diameter consisting of a solid solution of 20% CPTEG (poly1,8-bis[p-carboxyphenoxy]3,6-dioxaoctane) and 80% CPH (1,6-bis[p-carboxyphenoxy]hexane) and 0.036% whole killed bovine herpes virus-1 (75 μg) and 0.05% MPLA adjuvant (100 μg) by weight.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An implantable vaccine delivery device comprising:

(a) a container having a portion of its surface define porous openings that restrict intact cells from passing in and out of said container and that permit antibodies to pass in and out of said container, (b) a vaccine depot comprising an antigen and located within said container, and (c) a barrier material located within said container in a position wherein said antigen of said vaccine depot must travel through said barrier material to reach said porous openings, wherein said barrier material allows free antibodies and free antigen to pass through said barrier material, and wherein said barrier material prevents antibody-antigen complexes from passing through said barrier material.

2. The device of claim 1, wherein said container comprises a polyvinylidene difluoride membrane defining said porous openings.

3. The device of claim 1, wherein said porous openings are about 0.66 μm in diameter.

4. The device of claim 1, wherein said vaccine depot comprises 1,6-bis(p-carboxyphenoxy) hexane (CPH).

5. The device of claim 4, wherein said vaccine depot comprises CPTEG and CPH in a 20:80 ratio.

6. The device of claim 1, wherein said vaccine depot comprises 1,6-bis(p-carboxyphenoxy) hexane (CPH) and sebacic acid (SA).

7. The device of claim 6, wherein said vaccine depot comprises CPH and SA in a 80:20 ratio.

8. The device of claim 1, wherein said barrier material comprises collagen.

9. The device of claim 1, wherein said barrier material comprises hydroxyapatite.

10. The device of claim 1, wherein said barrier material defines pores about 40 to about 60 nm in diameter.

11. The device of claim 1, wherein said barrier material defines pores about 50 nm in diameter.

12. A method for vaccinating an animal, wherein said method comprising implanting a vaccine delivery device into said animal, wherein said vaccine delivery device comprises:

(a) a container having a portion of its surface define porous openings, (b) a vaccine depot comprising an antigen and located within said container, and (c) a barrier material located within said container, wherein cells within said animal are restricted from passing into said container, wherein antibodies within said animal are allowed to pass into said container, wherein said antigen of said vaccine depot must travel through said barrier material to reach said porous openings, wherein said barrier material allows free antibodies and free antigen to pass through said barrier material, and wherein said barrier material prevents antibody-antigen complexes from passing through said barrier material.

13. The method of claim 12, wherein said animal is a dog or cat.

14. The method of claim 12, wherein said antigen is gonadotropin-releasing hormone.

15. The method of claim 12, wherein said container comprises a polyvinylidene difluoride membrane defining said porous openings.

16. The method of claim 12, wherein said porous openings are about 0.22 μm in diameter.

17. The method of claim 12, wherein said vaccine depot comprises 1,8-bis(p-carboxyphenoxy)-3,6-dioxaoctane (CPTEG) and 1,6-bis(p-carboxyphenoxy) hexane (CPH).

18. The method of claim 17, wherein said vaccine depot comprises CPTEG and CPH in a 20:80 ratio.

19. The method of claim 12, wherein said vaccine depot comprises 1,6-bis(p-carboxyphenoxy) hexane (CPH) and sebacic acid (SA).

20. The method of claim 19, wherein said vaccine depot comprises CPH and SA in a 80:20 ratio.

21. The method of claim 12, wherein said barrier material comprises collagen.

22. The method of claim 12, wherein said barrier material comprises hydroxyapatite.

23. The method of claim 12, wherein said barrier material defines pores about 40 to about 60 nm in diameter.

24. The method of claim 12, wherein said barrier material defines pores about 50 nm in diameter.

* * * * *